(12) United States Patent
Kockott

(10) Patent No.: US 6,555,827 B1
(45) Date of Patent: *Apr. 29, 2003

(54) METHOD OF DETERMINING VARIATIONS IN THE PROPERTIES OF A SAMPLE

(76) Inventor: Dieter Kockott, Vogelsbergstrasse 27, 63456 Hanau (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 43 days.

(21) Appl. No.: 09/147,626
(22) PCT Filed: Aug. 6, 1997
(86) PCT No.: PCT/EP97/04294
§ 371 (c)(1), (2), (4) Date: Feb. 4, 1999
(87) PCT Pub. No.: WO98/07017
PCT Pub. Date: Feb. 19, 1998

(30) Foreign Application Priority Data

Aug. 10, 1996 (DE) .......... 196 32 349

(51) Int. Cl.⁷ .......... A61N 5/00; G21G 5/00
(52) U.S. Cl. .......... 250/492.1
(58) Field of Search .......... 250/492.1, 504 R, 250/493.1

(56) References Cited

U.S. PATENT DOCUMENTS

| | | | | |
|---|---|---|---|---|
| 3,693,020 A | * | 9/1972 | Ackerman Jr. | 250/219 R |
| 4,880,988 A | * | 11/1989 | Witt | 250/492.1 |
| 4,931,655 A | * | 6/1990 | Yoshida et al. | 250/492.1 |

FOREIGN PATENT DOCUMENTS

GB     2174800     * 11/1986

* cited by examiner

Primary Examiner—Bruce Anderson
(74) Attorney, Agent, or Firm—Dennison, Schultz & Dougherty

(57) ABSTRACT

A method for determining variations in properties of a sample exposed to artificial weathering includes the steps of irradiating the sample at a wavelength substantially in the range of 295 to 400 nm in an intensity at least five times that of solar radiation, and continuously measuring intensity, spectral distribution or both intensity and spectral distribution of radiation reflected by or passing through the sample.

10 Claims, 2 Drawing Sheets

METHOD OF DETERMINING VARIATIONS IN THE PROPERTIES OF A SAMPLE

Figure 1:
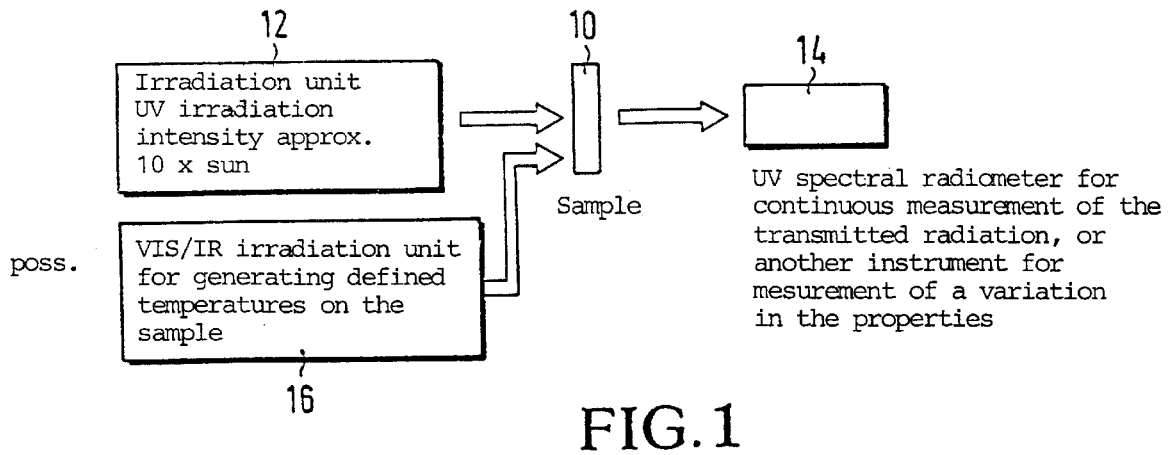

The invention relates to a method for determining variations in the properties of a sample exposed to artificial weathering, in particular consisting of a polymer material irradiated in a spectral range corresponding to solar radiation.

Methods for rapid weathering with commercial weathering equipment are known from, for example, DE 28 16 548 A1, EP 0 320 209 A2, DE-AS 1 904 097, U.S. Pat. Nos. 4,760,748, 4,874,952, DE 25 02 239 B2 or DE 35 04 793 C2. The known equipment is used for simulation of the ambient conditions, with the irradiation intensity and temperature being set to the maximum of the respective operating conditions. This permits a time acceleration that can have factors from 10 to 20 depending on the material. From GB 21 74 800 A, a device is known using which the radiation reflected from a lamp is continuously measured in order to ascertain color changes. The sample itself is disposed on a metal block that is set to a required temperature.

To permit a rapid analysis of plastics, a method and a device are proposed according to DE 43 31 296 A1 in which the plastic to be determined is irradiated with laser light, in order to then identify ablation/evaporation products using a Fourier transform/infra-red spectrometer.

To determine the absorption and laser resistance of optical layers, samples are arranged on a sensor and irradiated in accordance with DE 41 09 469 A1.

In order to determine the aging state of plastic objects regardless of their age, it is proposed in accordance with DE 31 21 928 A1 to illuminate the plastic objects with a light source that emits light in the entire visible spectral range, and then to determine the remission at at least one point on the surface of the plastic objects.

To rule out to a large extent an inadmissible temperature increase during the determination of variations in the properties of samples due to photochemical processes, it is known from—for example—DE 34 43 694 A1 how to cool the sample with air currents and fans or similar. With the known method, it is then possible to establish color differences, by a comparison of before and after the irradiation.

DE 40 02 985 A1 describes measures for avoiding unwelcome heating up of a sample during irradiation in a spectral range corresponding to solar radiation and with an irradiation intensity which is more than 30 times greater than that of solar radiation, by passing an air current over the surface of the sample.

According to DE 42 10 585 A1, the absorbed radiation used for assessing the aging process of the sample is calculated from a measured spectral absorption capacity of a sample and from the spectral distribution of the solar radiation.

Regardless of the large number of known methods and devices for rapid weathering of objects, the achievable acceleration factors are limited, in particular when it must be avoided that the sample is heated to an extent that other temperature-dependent influences occur in addition to photochemically determined aging processes. Furthermore, the samples are on principle not inspected until the treatment is complete.

The problem underlying the present invention is to develop a method for determining of variations in the properties of a sample exposed to artificial weathering such that high acceleration factors are achieved, in order to minimize the inspection times for quality checks. It should at the same time be assured that variations in the properties resulting from unwelcome temperature increases in the sample from radiation impinging thereon are ruled out or the heating of the samples can be set in a defined way regardless of the photochemically effective radiation, for example by additional IR radiation.

The problem is solved in accordance with the invention by a method for determining variations in the properties of a sample exposed to artificial weathering, in particular a sample of a polymer material that is irradiated in a spectral range corresponding to solar radiation and with an irradiation intensity that is at least about five times greater than that of solar radiation in the corresponding spectral range, with the variations in the properties of the sample being measured during the action of the radiation.

In a fundamental divergence from the prior art, the variation of the property of the sample during the artificial weathering is tracked by preferably continuous measurement of the transmitted or reflected radiation, for example by means of a UV spectral radiometer or another instrument for measurement of the variations in the properties. Here the method in accordance with the invention is suitable in particular for transparent or semi-transparent samples, i.e. directly applicable for films, free lacquer films or transparent covering lacquers. In the case of opaque samples, the change in the optical properties can also be measured in reflection. Alternatively, and as a further development worthy of emphasis, thin and still sufficiently transparent samples could be prepared from opaque materials.

In particular, the invention provides that the sample is irradiated with radiation in a wavelength range between approx. 295 and 400 nm, preferably between 295 and 320 nm. The sample can here be irradiated with an irradiation intensity corresponding to approximately ten times the solar radiation in the corresponding spectral range, without any marked temperature increase in the sample itself occurring. Here both the spectral range and the irradiation intensity should be set such that the sample is irradiated with a radiation in the UV wavelength range and with an intensity such that the sample is heated less than 3° C. during irradiation. Alternatively, the spectral range simulating solar radiation can be extended to 400 nm. As a result of the higher irradiation intensity, the heating up of a black body is then about 10° C.

With the teachings in accordance with the invention, unexpectedly high acceleration factors are achievable that permit a very rapid yet precise quality control, since falsifying influences in particular from temperature increases in the sample being inspected are ruled out. At the same time, the sample is subjected to radiation in a spectral range corresponding to the solar radiation that generally causes the variations in the properties of the materials being inspected.

If necessary, the sample can be subjected to visual or IR light in order to additionally set a defined temperature on or inside the sample without contact.

Further details, advantages and features of the invention are shown not only in the claims and in the features they contain—singly and/or in combination—but also in the following description of embodiments shown in the drawing.

Figure 3:
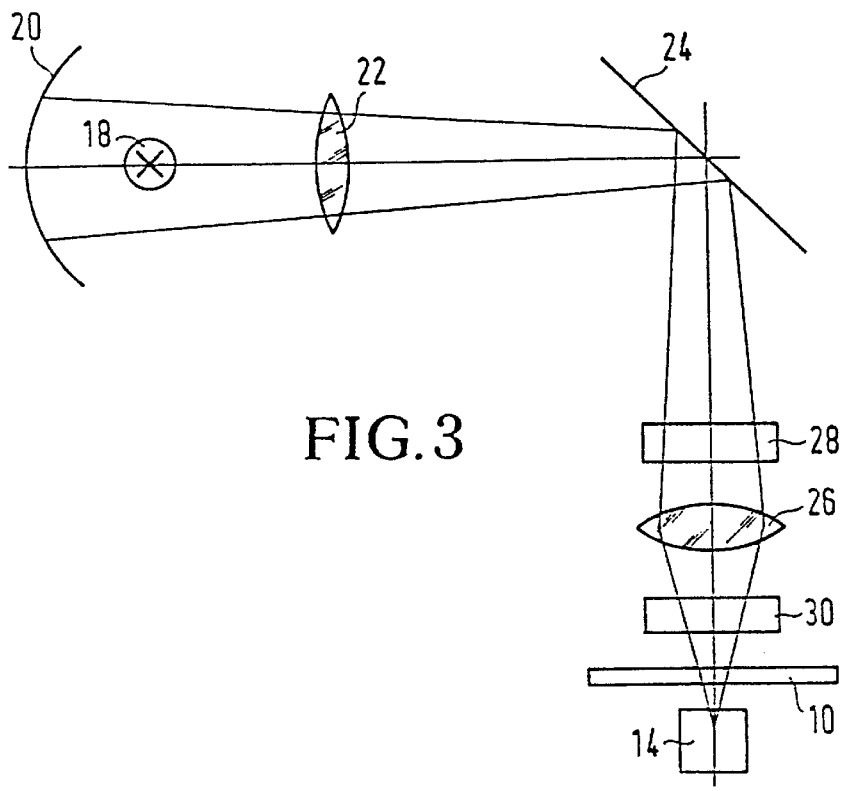
Figure 2:
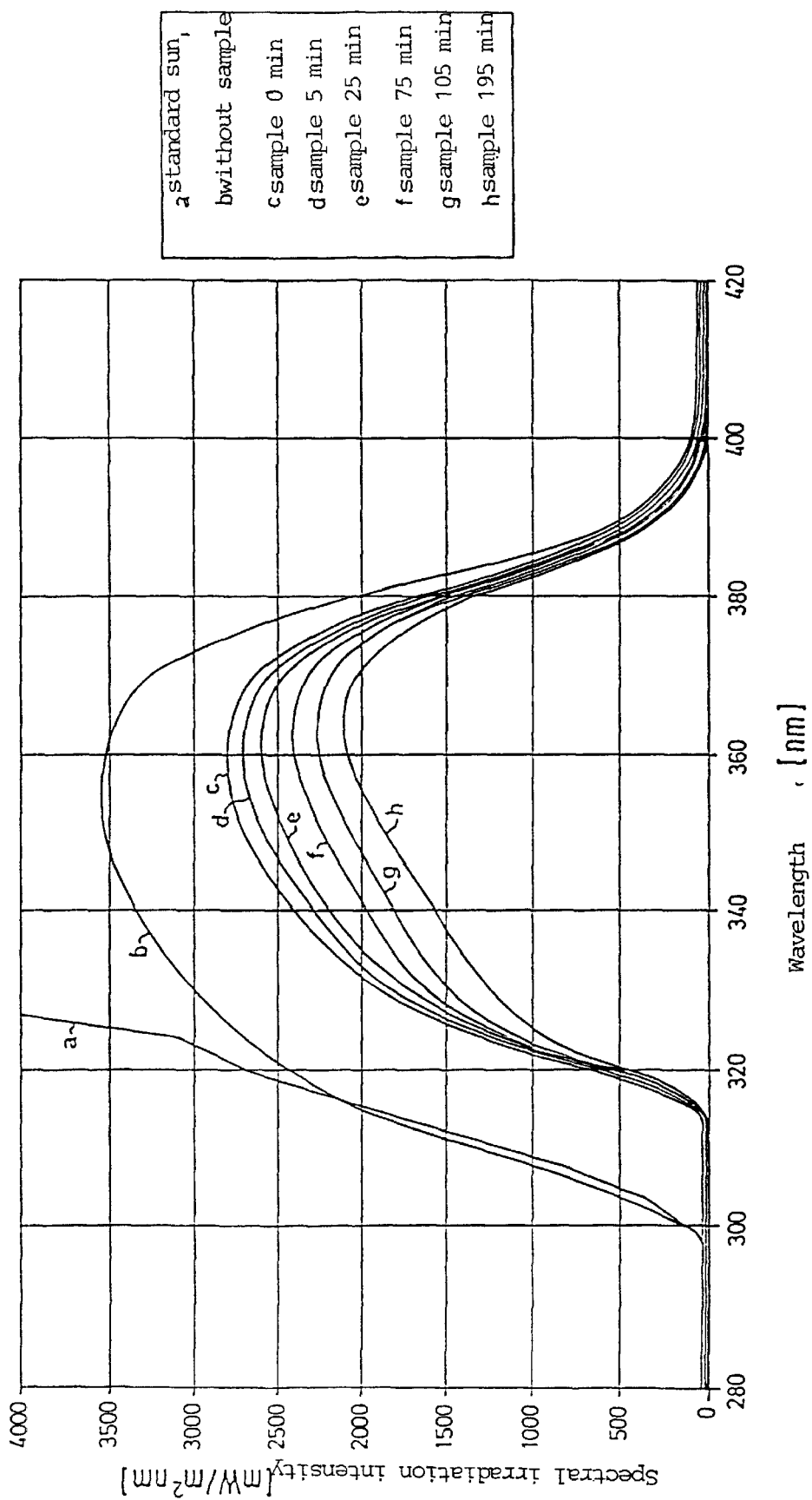

In the drawing,

FIG. 1 shows a principle view of an ultra-rapid weathering array,

FIG. 2 a spectral transmission of a sample after differing irradiation durations, and FIG. 3 shows an array for ultra-rapid weathering of a sample.

FIG. 1 shows purely in principle an array for ultra-rapid weathering of a sample 10 in the form of a polymer material. The sample 10, which is a transparent, possibly semi-transparent sample, is irradiated by an irradiation unit 12. The spectral distribution of the light from the irradiation unit 12 is between $295 \leq \lambda \leq 400$ nm, preferably between $295 \leq \lambda \leq 320$ nm, and corresponds to the solar radiation in this range, with the irradiation intensity in this wavelength range being however approximately ten times greater than that of the sun.

Behind the sample 10 is a UV spectral radiometer 14 for continuous measurement of the radiation passing through. It is of course possible to use another suitable instrument too instead of the UV spectral radiometer 14 in order to determine the spectral transmission $\tau(\lambda)$ of the sample 10 or another physical quantity, for characterization of variations in the properties of the sample material in a very short time.

If the sample 10 is to be set to a required temperature, it is furthermore possible to provide a visual or IR irradiation unit 16, using which a defined temperature can be generated on the sample 10.

An array suitable for practical use in the ultra-rapid weathering of in particular polymer materials that should be transparent or at least semi-transparent, in order to determine variations in the properties during irradiation on the basis of the transmitted radiation, is shown in FIG. 3. The radiation source can be a xenon lamp 18 with an output of—for example—150 W. The xenon lamp 18 is arranged in front of a spherical reflector 20. The radiation stemming directly from the xenon lamp 18 or from the spherical reflector 20 impinges via a first optical system on a selectively reflecting filter 24 from which the radiation passes via a second optical system 26 to the sample 10, behind which is arranged the UV spectral radiometer 14. The second optical system 26 is designed such that a ray with a diameter of approx. 10 mm is focused on the sample 10. Also connected in front of and/or behind the second optical system 26 are filters 28, 30 for generating the short-wave edge of the spectral distribution simulating the sunlight.

With a suitable array, it is possible to subject the sample 10 over an area with a diameter of—for example—10 mm to irradiation with an intensity ten times that of sunlight, with the spectral range in the wavelength range between 295 and 320 nm or between 295 and 400 nm corresponding to that of sunlight, without however any marked heating of the sample 10 itself occurring.

FIG. 2 reproduces the transmission change of a PPC film as a sample as a function of the irradiation duration. In this case, the spectral irradiation intensity passing through the sample is plotted against the wavelength.

As the illustration makes clear, both the intensity and the spectral distribution of the radiation passing through change in the course of irradiation. The change in the transmission $\tau(\lambda)$ of the material can accordingly be determined in a very short time using the method in accordance with the invention, before any change can be ascertained visually.

While in the embodiment the measurement of the variations in the properties using UV spectral radiometer is given as the preferred method, other analytical methods, for example IR spectroscopy, are also possible.

What is claimed is:

1. A method for determining variations in properties of a sample exposed to artificial weathering, comprising the steps of:

irradiating the sample-with radiation in a spectral range simulating solar radiation at a wavelength substantially in the range of 295 to 400 nm in an intensity at least five times that of solar radiation; and continuously measuring intensity vs. wavelength of radiation reflected by or passing through the sample.

2. Method according to claim 1, wherein the sample is transparent or semi-transparent, and radiation passing through the sample is determined.

3. Method according to claim 1, wherein the irradiating is limited such that the sample increases in temperature no more than about 10° C.

4. Method according to claim 3, wherein the increase in temperature is no more than about 3° C.

5. Method according to claim 1, wherein the intensity of the radiation is between five and ten times that of solar radiation.

6. Method according to claim 1, wherein the radiation impinging on the sample is focused on a diameter of 5–15 mm.

7. Method according to claim 6, wherein the radiation is focused on a diameter of 10 mm.

8. Method according to claim 1, additionally comprising directing a second source of radiation on the sample sufficient to heat the sample to a predetermined temperature.

9. Method according to claim 1, wherein the sample is a polymer.

10. Method according to claim 1, wherein the radiation is substantially in the range of 295 to 320 nm.

* * * * *